(12) United States Patent
Zarembo et al.

(10) Patent No.: US 7,865,248 B2
(45) Date of Patent: Jan. 4, 2011

(54) BIASING AND FIXATION FEATURES ON LEADS

(75) Inventors: Paul E. Zarembo, Vadnais Heights, MN (US); Brian D. Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1081 days.

(21) Appl. No.: 11/548,838

(22) Filed: Oct. 12, 2006

(65) Prior Publication Data

US 2007/0293925 A1    Dec. 20, 2007

Related U.S. Application Data

(63) Continuation-in-part of application No. 11/424,440, filed on Jun. 15, 2006.

(51) Int. Cl.
*A61N 1/05* (2006.01)

(52) U.S. Cl. .................................... 607/122

(58) Field of Classification Search ......... 607/115–130; 600/375; 128/785, 786
See application file for complete search history.

(56) References Cited

U.S. PATENT DOCUMENTS

| | | | | |
|---|---|---|---|---|
| 4,285,347 | A * | 8/1981 | Hess | 607/117 |
| 5,487,385 | A * | 1/1996 | Avitall | 600/374 |
| 5,755,765 | A * | 5/1998 | Hyde et al. | 607/122 |
| 5,800,482 | A * | 9/1998 | Pomeranz et al. | 607/101 |
| 5,931,864 | A | 8/1999 | Chastain et al. | |
| 5,951,597 | A * | 9/1999 | Westlund et al. | 607/126 |
| 5,991,668 | A | 11/1999 | Leinder et al. | |
| 6,006,122 | A * | 12/1999 | Smits | 600/373 |
| 6,132,456 | A * | 10/2000 | Sommer et al. | 607/127 |
| 6,178,356 | B1 | 1/2001 | Chastain et al. | |
| 6,385,492 | B1 | 5/2002 | Ollivier et al. | |
| 7,231,260 | B2 * | 6/2007 | Wallace et al. | 607/116 |
| 2003/0195603 | A1 | 10/2003 | Scheiner et al. | |
| 2003/0199961 | A1 * | 10/2003 | Bjorklund et al. | 607/126 |
| 2004/0054390 | A1 * | 3/2004 | Zarembo et al. | 607/122 |

* cited by examiner

*Primary Examiner*—Carl H. Layno
*Assistant Examiner*—Paula J Stice
(74) *Attorney, Agent, or Firm*—Faegre & Benson LLP

(57) ABSTRACT

A lead assembly for placement in a coronary vessel of the heart, the coronary vessel having a pericardial wall portion and a myocardial wall portion. The lead assembly comprises a lead body extending from a proximal end adapted for coupling to a pulse generator to a distal end adapted for implantation in the heart, an electrode positioned at the distal end of the lead body, and a loop biasing feature located at the distal end of the lead body. The loop biasing feature includes a resilient loop positioned to bias a portion of the electrode towards the myocardial wall portion of the coronary vessel by exerting a force against the pericardial wall portion. The loop biasing feature further includes a collar for coupling the loop biasing feature to the lead body. A method of implanting the lead assembly.

12 Claims, 9 Drawing Sheets

BIASING AND FIXATION FEATURES ON LEADS

RELATED APPLICATIONS

This is a continuation-in-part of pending U.S. patent application Ser. No. 11/424,440 titled LEAD WITH ORIENTATION FEATURE, filed Jun. 15, 2006, the entire disclosure of which is hereby incorporated herein by reference.

TECHNICAL FIELD

The present invention relates to medical devices and devices for securing a lead. More specifically, the invention relates to devices and methods for positioning and fixing a lead within a vessel of the heart.

BACKGROUND

Implantable medical devices for treating irregular contractions of the heart with electrical stimuli are well known in the art. Some of the most common forms of such implantable devices are defibrillators and pacemakers. Various types of electrical leads for defibrillators and pacemakers have been suggested in the prior art.

A broad group of leads may be characterized by the fact that they are placed transvenously. These leads are introduced into the patient's vasculature at a venous access site and travel through veins to the locations where the leads' electrodes will implant in or otherwise contact coronary tissue. One large subfamily of the group of transvenously-placed leads are those that are implanted in the endocardium (the tissue lining the inside of the heart) of the right atrium or ventricle. Another subfamily of the group of transvenously-placed leads are those that are placed in the branch vessels of the coronary venous system to stimulate the left ventricle.

The treatment of heart failure often requires left ventricular stimulation either alone or in conjunction with right ventricular stimulation. For example, cardiac resynchronization therapy (also commonly referred to as biventricular pacing) is an emerging treatment for heart failure, which requires stimulation of both the right and the left ventricle to increase cardiac output. Left ventricular stimulation requires placement of a lead in or on the left ventricle in the lateral or posterior-lateral aspect/region of the heart. One technique for left ventricular lead placement is to advance a lead endovenously into the coronary sinus and then advance the lead through a branch vein onto the surface of the left ventricle so as to stimulate the myocardium of the heart. Although methods and tools have been developed to navigate the lead through the vasculature, and in particular to direct the lead into a selected branch vessel of the coronary sinus, it can be difficult to orient the electrodes to face and stimulate the myocardium. If the electrodes come into contact with the pericardial wall portion of the branch vessel, rather than the myocardial wall portion, a degraded site for sensing and pacing may result.

The left ventricle beats forcefully as it pumps oxygenated blood throughout the body. Repetitive beating of the heart, in combination with patient movement, can sometimes dislodge the lead from the branch vessel. Over time, the electrodes may lose contact with the heart muscle, or move from their original location and orientation.

There is a need for an improved lead and method of implantation for orienting the lead into the coronary sinus branch vessels such that the lead electrodes contact the myocardium, and also to provide controlled fixation and removal of the lead.

SUMMARY

In one embodiment, the present invention is a lead assembly for placement in a coronary vessel of the heart. The coronary vessel has a pericardial wall portion and a myocardial wall portion. The lead assembly comprises a lead body extending from a proximal end adapted for coupling to a pulse generator to a distal end adapted for implantation in the heart, an electrode positioned at the distal end of the lead body, and a loop biasing feature located at the distal end of the lead body. The loop biasing feature includes a resilient loop positioned to bias a portion of the electrode towards the myocardial wall portion of the coronary vessel by exerting a force against the pericardial wall portion. The loop biasing feature further includes a collar for coupling the loop biasing feature to the lead body.

In another embodiment, the present invention is a lead assembly for placement in a coronary vessel of the heart. The coronary vessel has a pericardial wall portion and a myocardial wall portion. The lead assembly comprises a lead body extending from a proximal end adapted for coupling to a pulse generator to a distal end adapted for implantation in the heart. The lead body includes a lumen extending from the proximal end to the distal end. An electrode is positioned at the distal end of the lead body. A loop biasing feature is located at the distal end of the lead body. The loop biasing feature includes a resilient loop positioned to bias a portion of the electrode towards the myocardial wall. A cord is coupled to the loop and extends to the proximal end of the lead body. A tensile force applied to the cord causes the loop to flatten towards the lead body and a portion of the loop to slide into the lumen.

In yet another embodiment, the present invention is a method of implanting a lead in a coronary vessel of the heart. The coronary vessel has a pericardial wall portion and a myocardial wall portion. The method comprises providing a lead body extending from a proximal end adapted for coupling to a pulse generator to a distal end adapted for implantation in the heart, an electrode positioned at the distal end of the lead body, and a loop biasing feature located at the distal end of the lead body. The loop biasing feature includes a resilient loop. The resilient loop is compressed towards the lead body by inserting the lead into a guide catheter. The distal end of the lead body is advanced into the coronary vessel to a fixation location. The electrode is biased towards the myocardial wall portion of the coronary vessel by engaging the loop biasing feature.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
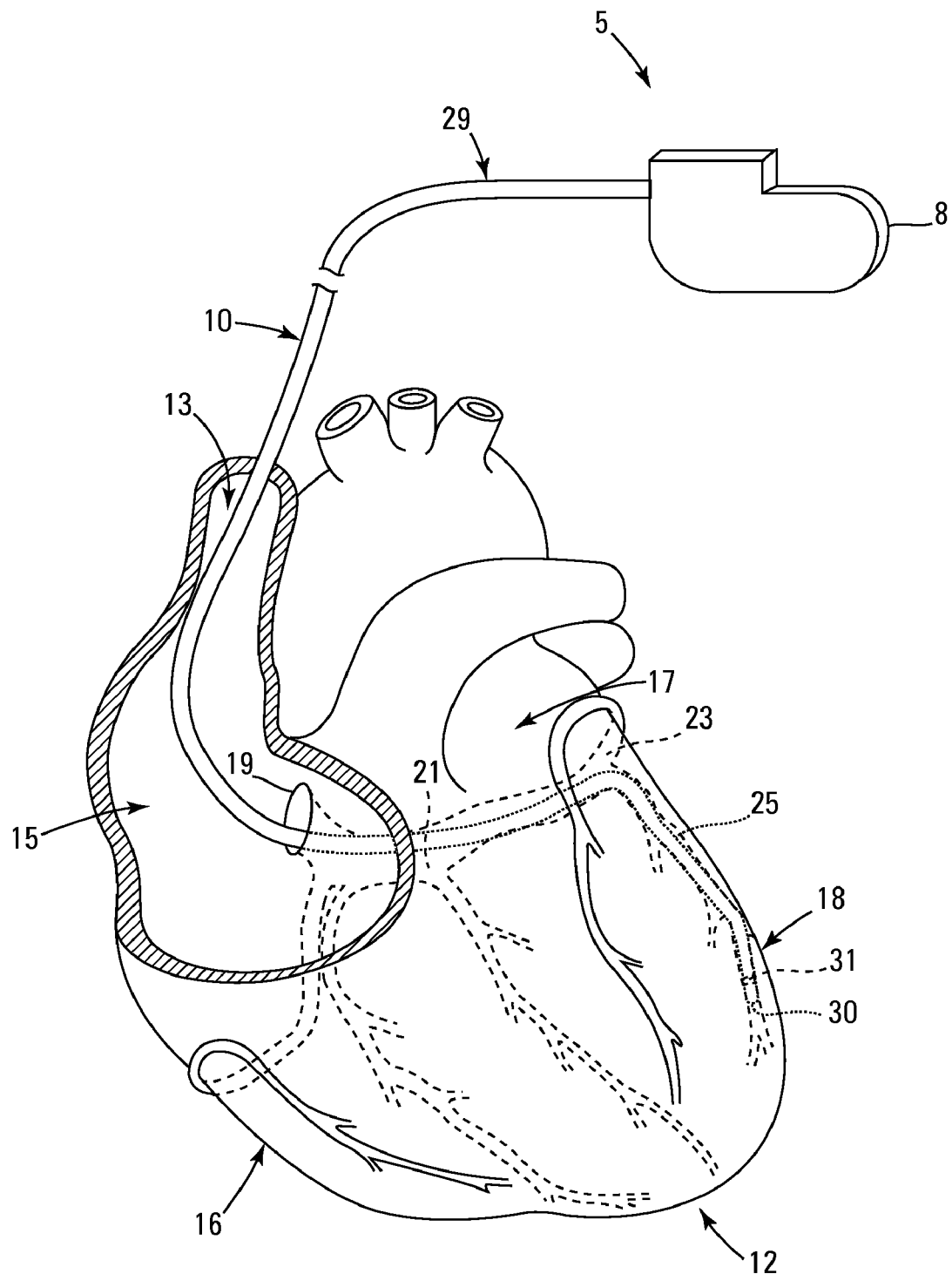
FIG. 1 shows an exemplary implantable medical device in relation to a heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 5 including a pulse generator 8 coupled to an exemplary lead assembly 10 deployed in a patient's heart 12 from a superior vena cava 13. As shown, the heart 12 includes a right atrium 15 and a right ventricle 16, a left atrium 17 and a left ventricle 18, a coronary sinus ostium 19 in the right atrium 15, a coronary sinus 21, and various cardiac vessels including a great cardiac vein 23 and other branch vessels of the coronary sinus 21 including an exemplary branch vessel 25.

Figure 2:
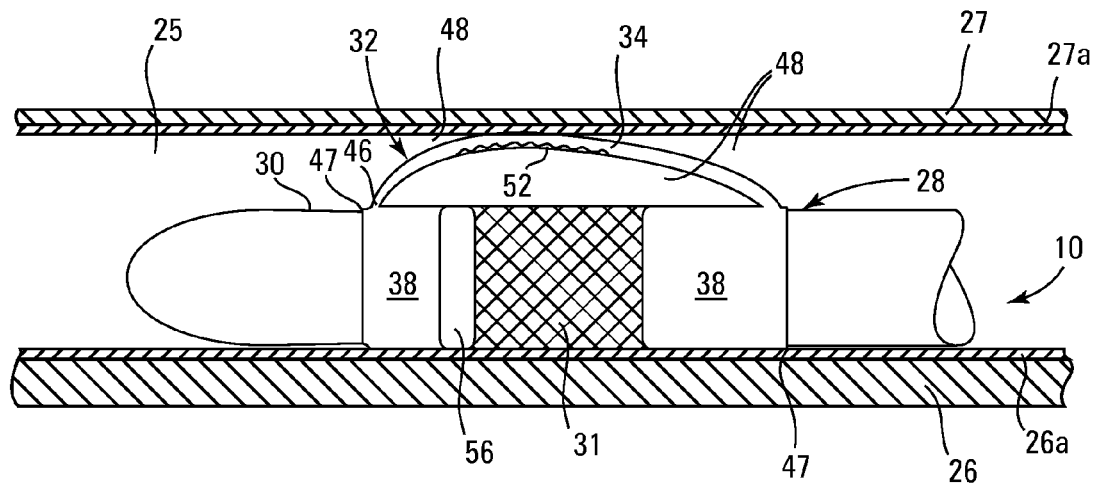
FIG. 2 shows a side view of the distal end of a lead assembly according to one embodiment of the present invention in relation to a branch vessel of the coronary sinus.

FIG. 2 shows a portion of the lead assembly 10 according to one embodiment of the present invention. The lead assembly 10 is shown implanted in the branch vessel 25. The branch vessel 25 has a myocardial wall portion 26a nearer to a myocardium 26 of the heart 12 and a pericardial wall portion 27a nearer to a pericardium 27 of the heart 12. The lead assembly 10 includes a lead body 28 extending from a proximal end 29 (see FIG. 1) adapted for coupling to the pulse generator 8 to a distal end 30 adapted for insertion into the heart 12. An electrode 31 is positioned at the distal end 30 of the lead body 28 for pacing and sensing electrical stimuli. While the lead assembly 10 is shown as a monopolar-type lead having a single electrode 31, it is also contemplated that one or more electrodes may be positioned on the lead body 28 to allow for unipolar, bipolar or multi-polar pacing and sensing. It is also contemplated that one or more electrodes may be positioned on the lead body 28 to allow pacing and sensing at a selected electrode in a preferred position.

The lead assembly 10 further includes a loop biasing feature 32 at the distal end 30 of the lead body 28. In the embodiment generally shown in FIG. 2, the loop biasing feature 32 includes a resilient loop 34 of material protruding from the lead body 28. As shown in FIG. 2, the loop 34 forms a closed curve with the lead body 28. The size of the lead biasing feature 32 and the loop 34 may vary with respect to the size of the lead assembly 10. In one embodiment, the loop 34 extends a distance between approximately 0.003 and 0.250 inches from the lead body 28. In one embodiment, the loop 34 has a radius between approximately 0.025 and 10.0 inches. The loop 34 may have an included angle between approximately 10 and 179 degrees.

The loop 34 is resilient. It rebounds or springs back into shape after bending or being compressed. The resilient loop 34 allows the loop biasing feature 32 to exert a force against the pericardial wall portion 27a. In one embodiment, the loop biasing feature exerts a force between 1 and 800 grams when fully compressed. The force exerted by the loop biasing feature 32 when the loop 34 is extended is a function of the vessel size and the loop shape and size. The loop biasing feature 32 may be formed from a material having a predetermined shape. The loop biasing feature 32 may be made of a variety of materials, including, for example, molded or extruded silicone rubber, polyurethane or other polymeric materials. The loop biasing feature 32 may also be made of a flexible coil, cable or wire, coated or uncoated with a material as described above. In other embodiments, the loop biasing feature 32 can be made of any material and have any shape that is capable of exerting a force against the pericardial wall portion 27a.

In the embodiment illustrated in FIG. 2, the loop biasing feature 32 further includes a collar 38 coupling the loop 34 to the lead body 28. The collar 38 is initially slidable along the lead body 28 so as to selectively position the loop 34 at various locations along the lead body 28, as well as to permit addition and/or removal of the loop biasing feature 32 from the lead body 28. In the illustrated embodiment, a groove 47 is formed in the lead body 28 for receiving the collar 38 and retaining the collar 38 in position. The groove 47 may be sized as shown such that the collar 38 is isodiametric with the remainder of the lead body 28. In other embodiments, an adhesive or other fixator (not shown) may be employed to fix the collar 38 to the lead body 28, or the loop biasing feature 32 may be otherwise mechanically coupled to the lead body 28, or integrally formed with the lead body 28.

The loop biasing feature 32 protrudes from the lead body 28 in such a manner as to frictionally engage the pericardial wall portion 27a of the branch vessel 25 as shown in FIG. 2. The loop biasing feature 32 thus biases the electrode 31 away from the pericardial wall 27a and towards the myocardial wall 26a of the branch vessel 25. In addition, the loop biasing feature 32 increases the frictional force between the lead body 28 and the branch vessel 25, thus helping to fix the lead body 28 within the branch vessel 25.

In the illustrated embodiment, the loop biasing feature 32 is positioned adjacent to the electrode 31 so as to bias a portion of the electrode 31 opposite the loop 34 towards the myocardial wall 26a. In other embodiments, however, one or more loop biasing features 32 may be positioned at various locations on the lead body 28, not necessarily adjacent to the electrode 31, so as to bias the one or more electrodes 31 towards the myocardial wall 26a. In other embodiments, the loop biasing features 32 may be positioned at the same distal location on the lead body 28 (as shown in FIGS. 8 and 9A-9C) or may be staggered along the length of the lead body 28 (not shown). The position of the loop biasing feature 32 may therefore be selected to take advantage of the complex shape of the branch vessel 25 so as to bias and fix the electrode 31 towards the myocardial wall 26a. In other embodiments, a loop biasing feature 32 may include one or more loops 34, one or more collars 38, or any variation in the number of loops 34 and collars 38.

Figure 3:
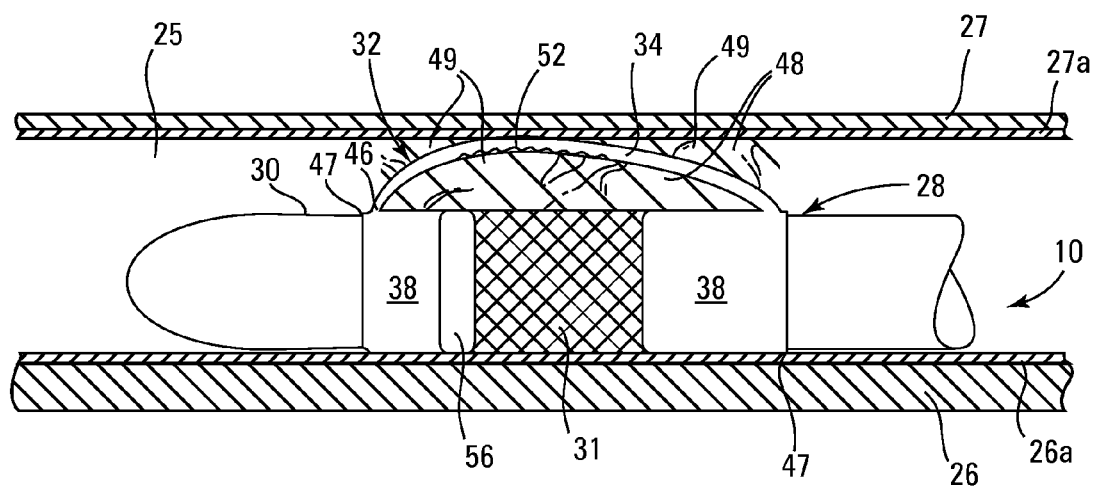
FIG. 3 shows a side view of the distal end of the lead assembly of FIG. 2 detailing tissue in-growth.

The loop biasing feature 32 defines a tissue in-growth area 48 between the lead body 28 and the loop 34. The tissue in-growth area 48 is an open region into which scar tissue or clotting material may grow upon implantation, further fixing the lead assembly 10 in place. FIG. 3 shows tissue 49, which has grown into the tissue in-growth area 46. In some embodiments, a pharmaceutical agent, such as a clotting agent, or other therapeutic treatment 52 is embedded or coated onto the loop biasing feature 32, as shown in FIGS. 2 and 3, or nearby on the lead body 28, to facilitate tissue in growth on and about the tissue in-growth area 48. One such exemplary clotting agent is the QuikClot® brand hemostatic agent (available from Z-Medica Corporation of Wallingford, Conn.). The loop 34 can be coated with or encapsulated by a drug so as to be a delivery mechanism for delivering drugs or other therapeutic treatments such as steroids to the heart 12 (not shown). In FIG. 3, the tissue 49 is shown completely extending from the pericardial wall 27a to the lead body 28 in the area of the loop 34, but in other embodiments, the tissue 49 need not extend completely from the pericardial wall 27a to the lead body 28. The tissue 49, for example, may partially encompass the loop 34. In other embodiments, the lead assembly 10 may further include a drug collar 56 on the lead body 28 for delivering drugs or other therapeutic treatments such as steroids to the heart 12.

Figure 4:
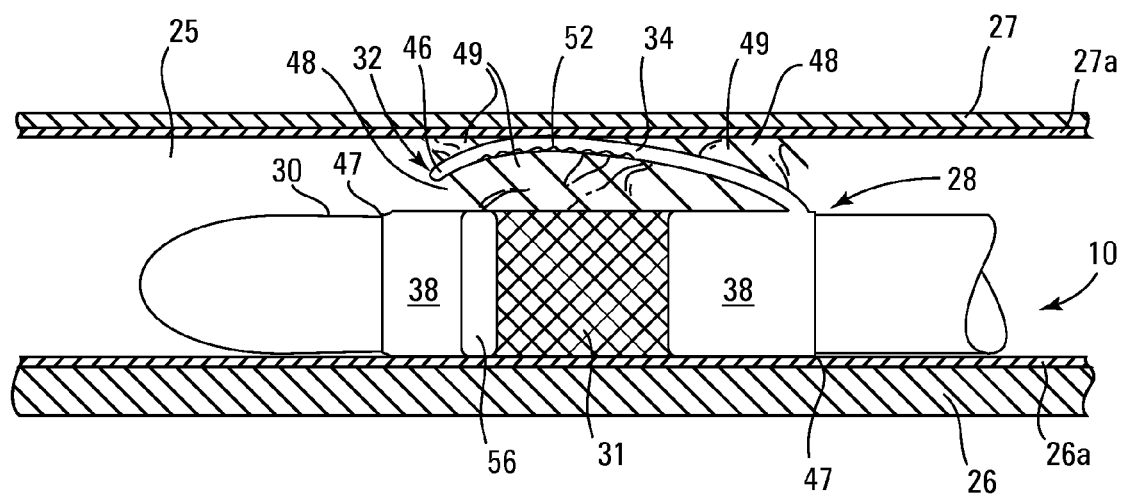
FIG. 4 shows a side view of the distal end of the lead assembly of FIG. 3 partially removed from the branch vessel.

In the illustrated embodiment, the loop biasing feature 32 includes an optional necked down region 46 of the loop 34 connecting the loop 34 to the collar 38. As shown in FIGS. 2 and 3, the necked down region 46 of the loop 34 is thinner than the remainder of the loop 34, so as to break at a pre-determined axial load. In one embodiment, the predetermined axial load can be between 1 and 800 grams. In another embodiment, the predetermined axial load can be 100 grams. By breaking the loop 34, as illustrated in FIG. 4, the biasing and frictional force between the lead assembly 10 and the branch vessel 25 is reduced and the loop 34 can be pulled out of the tissue 49 surrounding the loop 34. This can be used to disengage the loop biasing feature 32 from the branch vessel 25 to facilitate removal of the lead assembly 10. In the embodiment generally illustrated in FIGS. 2-4, the necked down region 46 is at an end of the loop 34. In other embodiments, the necked down region 46 may be located anywhere on the loop biasing feature 32, including, for example, in the center of the loop 34. The loop 34 can pull off of the lead body 28 or out of the lead body 28. The loop 34 can remain connected to the lead body 28 after the necked down region 46 has been broken.

Figure 5A:
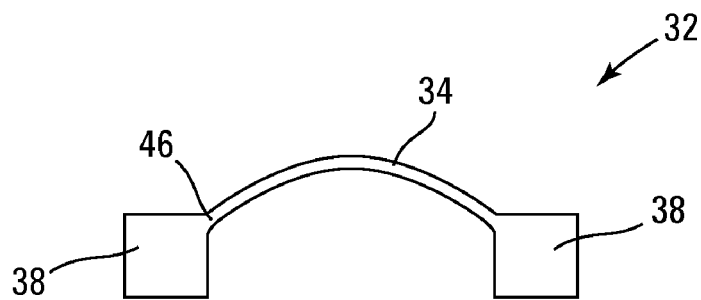
FIGS. 5A-5D show a loop biasing feature according to alternative embodiments of the present invention.
Figure 5B:
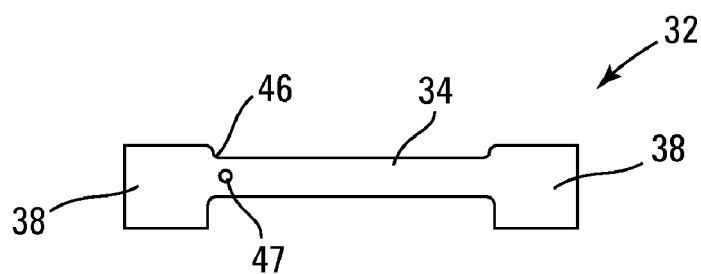
Figure 5C:
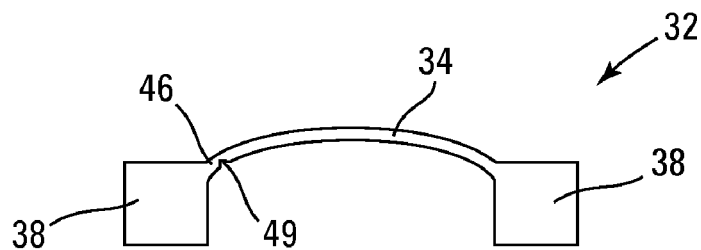
Figure 5D:
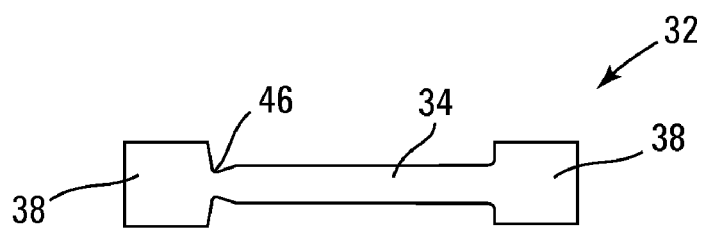

FIGS. 5A-5D show alternative embodiments of the loop biasing feature 32. In the embodiment shown in the side view of FIG. 5A, the necked down region 46 has the same dimensions as the loop 34, but has been weakened by heat, radiation, or any other suitable means for weakening the necked down region 46. Alternatively, the loop biasing feature 32 can also include a hole 47 in the necked down region 46, as shown in the top view of FIG. 5B. This hole 47 weakens the loop 34, thus reducing the axial force necessary to break the loop 34. The side view of FIG. 5C illustrates an alternative embodiment of the loop biasing feature 32 where the necked down region 46 includes a notch 49. The top view shown in FIG. 5D illustrates an embodiment where the necked down region 46 is thinner in a plane parallel to the top of the loop biasing feature 32. Any combination of holes 47, notches 49, and necked down regions 46 can be used to alter the axial force required to break the loop 34. In an alternative embodiment, the loop 34 does not include a necked down or weakened region 46, and the cross-sectional area of the loop 34 controls the axial force needed to break the loop 34.

Figure 6:
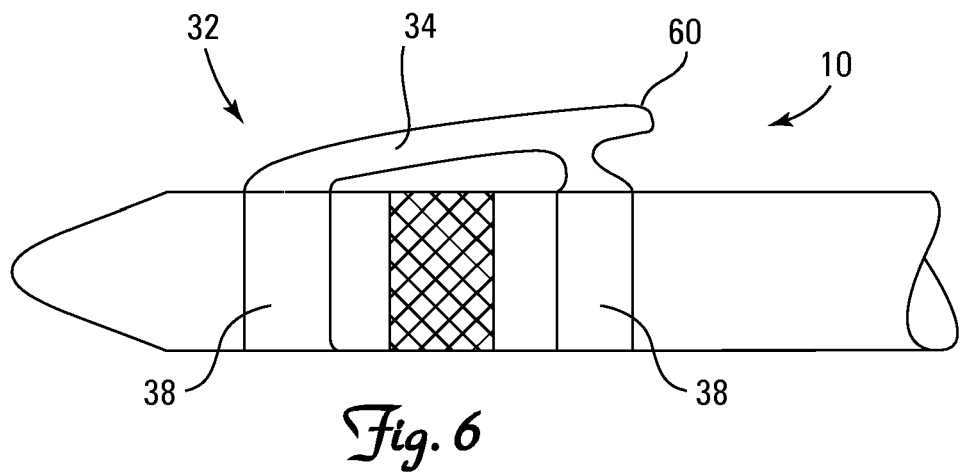
FIG. 6 shows a side view of the distal end of a lead assembly according to another embodiment of the invention.
Figure 7:
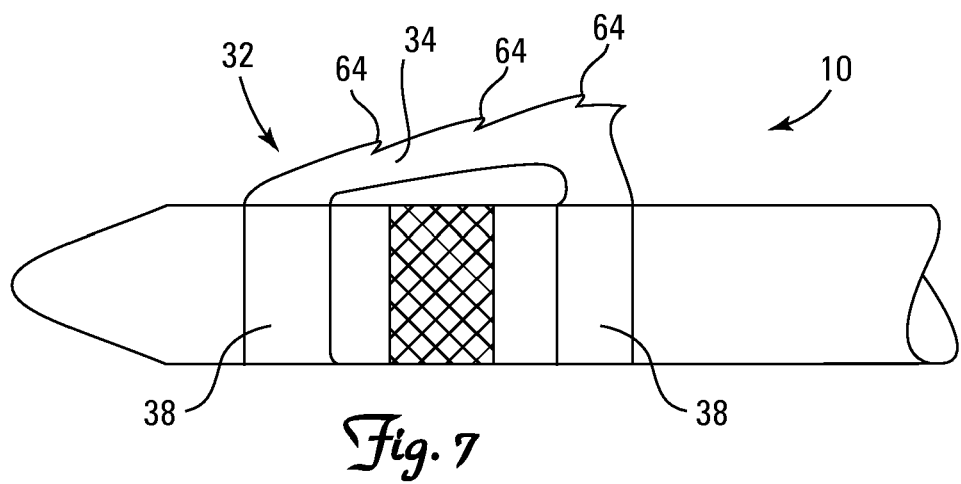
FIG. 7 shows a side view of the distal end of a lead assembly according to yet another embodiment of the invention.

FIGS. 6 and 7 show additional embodiments of the loop biasing feature 32 where the loop biasing feature 32 includes a fixation structure. For example, the loop 34 may be formed with a tine 60, as shown in FIG. 5, or scales 64, as shown in FIG. 6, to increase fixation or friction between the loop biasing feature 32 and the branch vessel 25. These features may reduce unintended dislodgement of the lead assembly 10 from a selected fixation location.

Figure 8A:
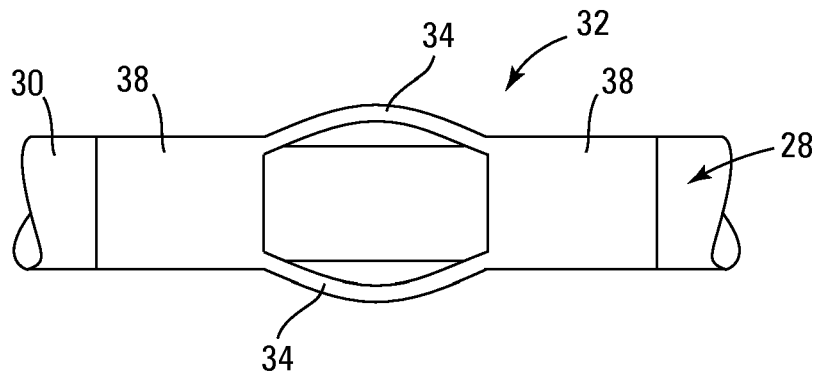
FIGS. 8A-8B show a loop biasing feature according to yet another alternative embodiment of the present invention.
Figure 8B:
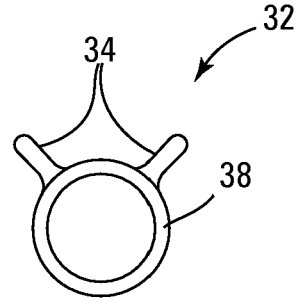

FIGS. 8A and 8B show yet another alternative embodiment of the loop biasing feature 32 where the loop biasing feature 32 includes two loops 34. In some circumstances, the groove along the heart 12 where the vessel 25 lies may be somewhat oval. As a result, certain positions of loops 34 around the circumference of the lead body 28 may preferentially orient the lead assembly 10 and loop biasing feature 32 into a position where the electrode 31 faces towards the heart 12 and the loops 34 face away from the heart 12. This can result in better electrical contact with the heart 12. The location of the loop or loops 34 around the circumference of the lead body 28 may therefore be critical. FIGS. 8A-8B depict an embodiment for such orientation. Although two loops 34 are shown in FIGS. 8A and 8B, the loop biasing feature 32 could include any number of loops 34.

Figure 9A:
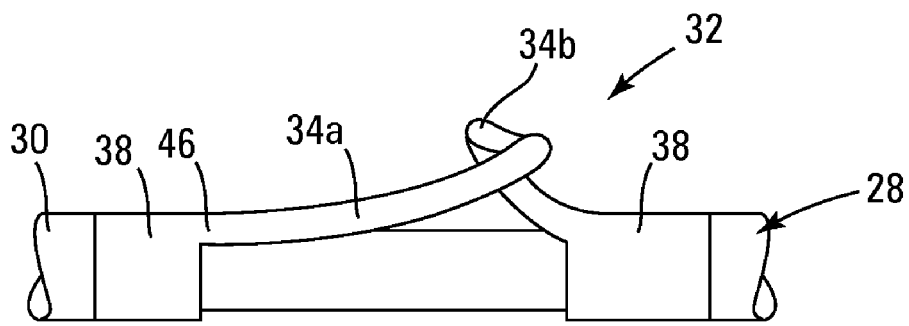
FIGS. 9A-9C show a loop biasing feature according to an alternative embodiment of the present invention.
Figure 9B:
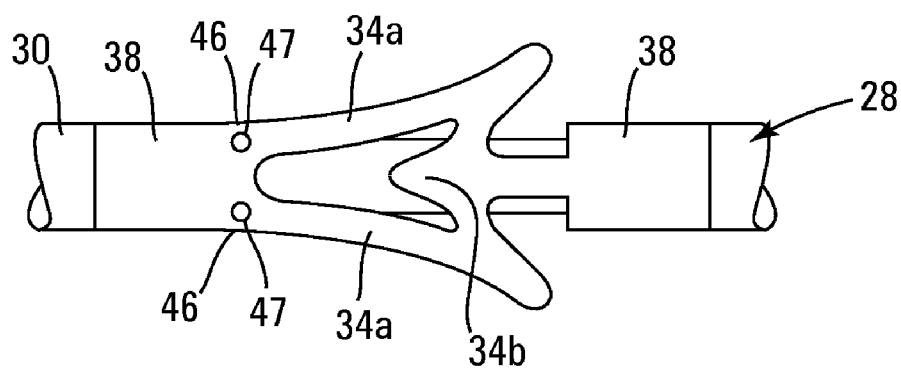
Figure 9C:
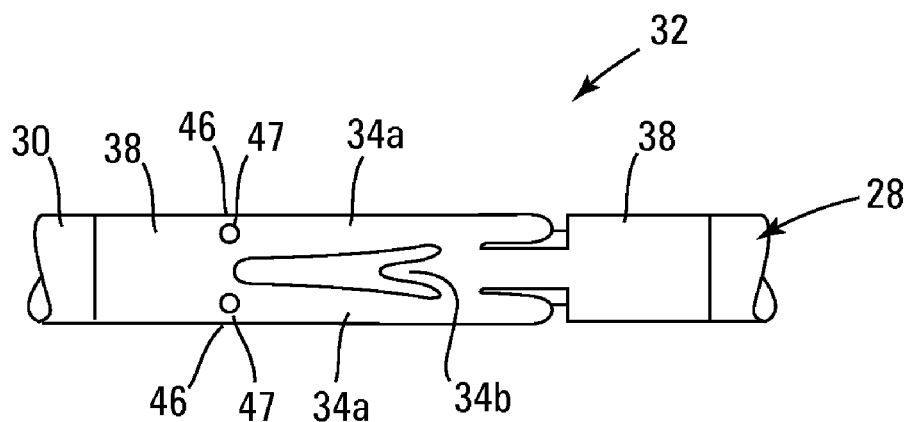

FIGS. 9A-9C show another alternative embodiment of the loop biasing feature 32 where the loop biasing feature 32 includes more than one loop 34. In this embodiment, the loop biasing feature 32 includes two loops 34a and a loop 34b interposed between the loops 34a. The loops 34a, 34b are similar to the tines 60. The loops 34a resist motion of the lead tip 30 in the proximal direction and the loop 34b resists motion of the lead tip 30 in the distal direction. As shown in FIG. 9C, the loops 34 folds down into down onto the lead body 28 so that it can more easily slide thru a catheter (not shown) and vessels 25, or deploy in a more predictable manner. The loop biasing feature 32 may optionally include holes 47 located in the necked down region 46 to facilitate removal of the lead assembly 10. Although the embodiments illustrated in FIGS. 8A-8B and 9A-9C show two loops 34, the loop biasing feature 32 could have additional loops 34 having any desired shape and optionally including a necked down region 46, a hole 47, or a notch 49.

Figure 10:
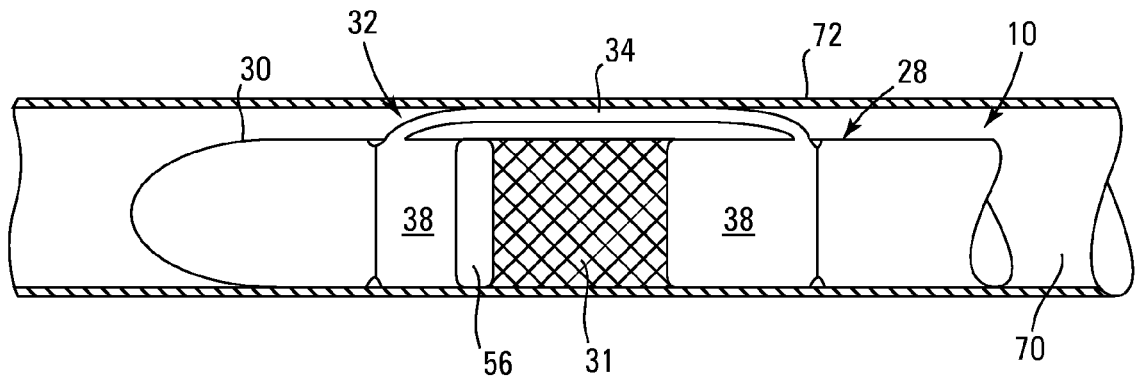
FIG. 10 shows a side view of a distal end of a lead assembly according to one embodiment of the present invention positioned within a guide catheter.
Figure 11:
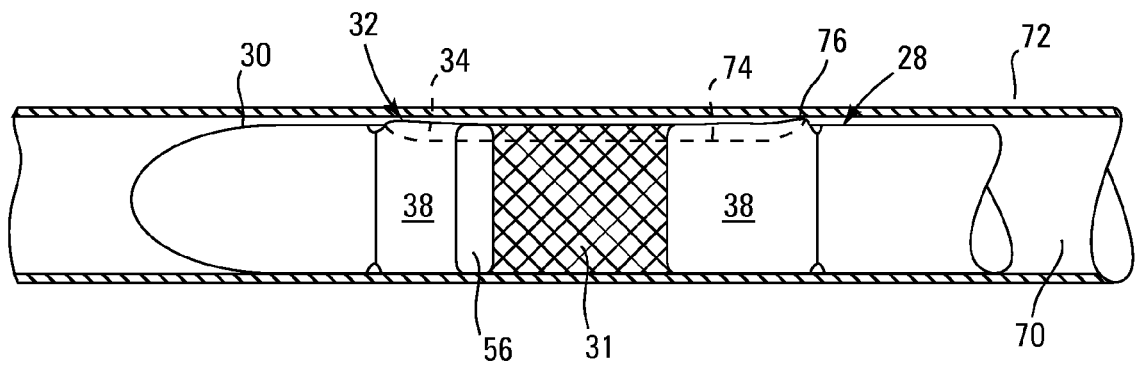
FIG. 11 shows a side view of a distal end of a lead assembly according to another embodiment of the present invention positioned within a guide catheter.

The lead assembly 10 may be delivered into the branch vessel 25 with a variety of techniques as are known in the art, including through the use of a guide catheter and/or stylet. FIG. 10 shows an embodiment of the lead assembly 10 positioned for delivery into the branch vessel (not shown) through a lumen 70 of a guide catheter 72. A stylet, guidewire, or another catheter (not shown) may be used to advance the lead assembly 10 through the lumen 70. As the lead assembly 10 passes through the lumen 70, the loop 34 flattens down against the lead body 28. Thus, the diameter of the guide catheter 72 may be sized smaller than the combined diameter of the lead body 28 and the loop 34. In one embodiment, as illustrated in FIG. 11, a groove 74 is formed into an outer surface 76 of the lead body 28 to receive the flattened loop 34. This further reduces the diameter of the lead assembly 10 and of the guide catheter 72. In the illustrated embodiment, the groove 74 extends over the electrode 31. In other embodiments, the loop biasing feature 32 may be positioned on the lead body 28 such that the loop 34 and/or the groove 74 do not pass over the electrode 31 (not shown).

Figure 12A:
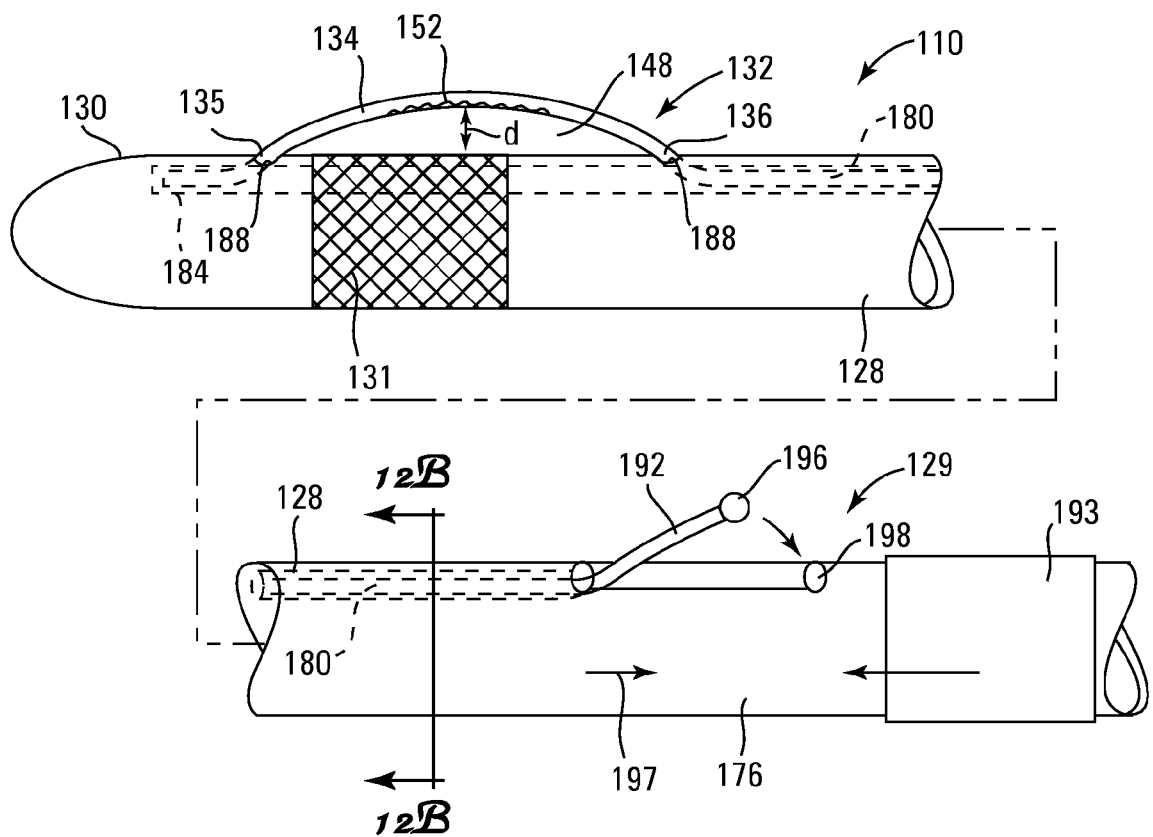
FIG. 12A shows a side view of a lead assembly according to yet another embodiment of the invention.
Figure 12B:
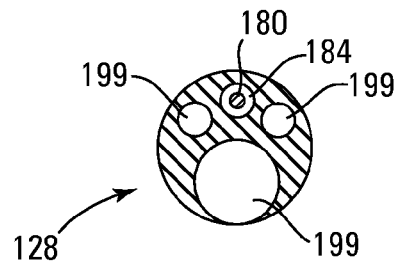
FIG. 12B shows a cross-sectional view of the lead assembly of FIG. 12A taken along line 12A-12A.

FIGS. 12A and 12B show a lead assembly 110 according to another embodiment of the invention. The lead assembly 110 includes a lead body 128 extending from a proximal end 129 adapted for coupling to a pulse generator (not shown) to a distal end 130 adapted for insertion into the heart 12. An electrode 131 is positioned at the distal end 130 of the lead body 128.

The lead assembly 110 further includes a loop biasing feature 132 at the distal end 130 of the lead body 128. The loop biasing feature 132 includes a loop 134 of cord, filament or cable material protruding from the lead body 128. In the illustrated embodiment, the loop 134 has a distal end 135 fixed to the lead body 128 by, for example, adhesive, a crimp tube, compressive fit, or any other suitable manner (not shown). A proximal end 136 of the loop 134 is coupled to a cord 180 extending through a cord lumen 184 formed in the lead body 128. The proximal and distal ends 136, 135 of the loop 134 exit and enter the cord lumen 184 through a pair of ports 188 in the lead body 128. A proximal end 192 of the cord 180 is coupled to an optional grasp feature 196. A pocket 198 is provided in an outer surface 176 of the lead body 128 for receiving the grasp feature 196. A slidable tube 193 is positioned over the lead body 128 for covering the proximal end 192 of the cord 180 and the pocket 198. In one embodiment, as illustrated in FIG. 11, a groove 174 is formed in the outer surface 176 of the lead body 128 for receiving the flattened loop 134. In an alternative embodiment where the loop distal end 135 is fixed to the lead body 128 through an adhesive, crimp tube, compressive fit, or any other suitable manner, a tensile force applied to the cord 180 causes the loop distal end to detach, thus facilitating removal of the lead assembly 110.

In some embodiments, the loop 134 and the cord 180 are not separate components, but rather the loop 134 is formed of a portion of the cord 180 which is sufficiently rigid to bias the lead body 128 towards the epicardium 27 and the myocardium 26. As previously discussed, in some embodiments, pharmaceutical agents 152 can be added to the lead assembly 110 to facilitate tissue in-growth into a tissue in-growth area 148 defined between the loop 134 and the lead body 128. Alternatively, the lead body 128 could include a surface treatment such as a plasma treatment.

The loop 134 protrudes from the lead body 128 in such a manner as to engage the pericardial wall 27a as previously described. The loop biasing feature 132 thus biases the electrode 131 towards the myocardial wall 26a and also helps to fix the lead body 128 within the branch vessel 25 (not shown). A proximally directed force exerted on the grasp feature 196, as illustrated by arrow 197, tensions the cord 180, thereby flattening the loop 134 towards the lead body 128 for implanting, revising or removing the lead assembly 110. Stated another way, the cord 180 permits the loop biasing feature 132 to be neutralized by reducing a distance d between the loop 134 and the exterior surface 176 of the lead body 128. In other embodiments, the loop 134 twists or bends on itself so as to flatten towards the lead body 128 during implantation.

The cord 180 is typically formed of a lubricious material such as ethylene tetrafluoroethylene (ETFE), polytetrafluoroethylene (PTFE) or expanded polytetrafluoroethylene (ePTFE) or other strong polymer such as polyester, aramid, Kevlar®, or is coated with such a material so as to reduce friction between the cord 180 and the cord lumen 184. Examples of other suitable materials include coextruded PTFE/Kevlar®, and can be polymer coated cable or nitinol wire. This reduces the axial force necessary to tension the cord 180 so as to neutralize the loop biasing feature 132 and reposition or extract the lead assembly 110.

FIG. 12B shows a cross-sectional view of the lead body 128, showing the cord 180 and cord lumen 184. As illustrated in FIG. 12B, the lead body 128 may include additional lumens 199 for uses such as delivery of payloads or receiving a conductive member. The cord 180 and/or the electrode 131 can be radio-opaque to allow the implanter to visualize deployment and electrode orientation with respect to the myocardial wall 26a to provide optimal or desirable orientation.

Figure 13:
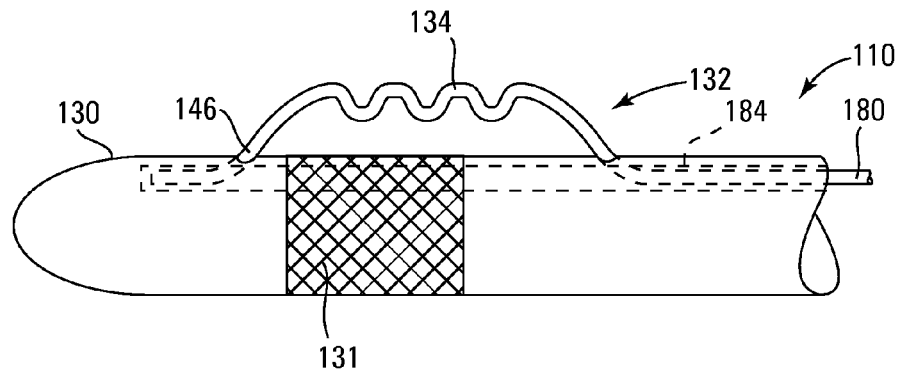
FIG. 13 shows a side view of a distal end of a lead assembly according to another embodiment of the invention.

In the embodiment illustrated in FIG. 12A, the loop 134 is preformed with the curvature shown. The loop 134 is thus biased outwardly into the loop shape protruding from the lead body 128 by virtue of the preformed curvature. In other embodiments, the loop 134 may be preformed with different shapes than that shown in FIG. 12A. For example, the loop 134 may be preformed with multiple curvatures (as shown in FIG. 13), or may have a variable cross-section along the length of the loop 134 (not shown). In alternative embodiments, the loop 34 can have a thickness such that the loop 34 shields or otherwise insulates a portion of the electrode 31 to prevent stimulation of the nerves located near the pericardium 27 and coronary vessels or the diaphragm (not shown).

Figure 14:
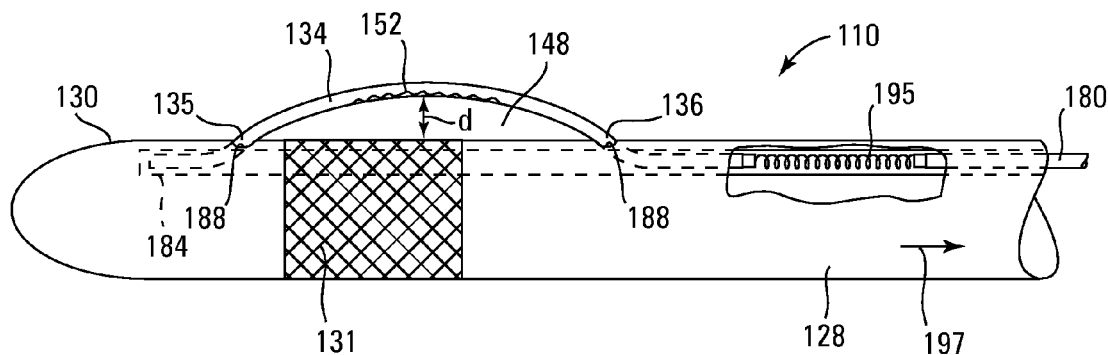
FIG. 14 shows a side view of a distal end of a lead assembly according to another embodiment of the present invention.

In yet another embodiment, the loop 134 is biased outward by a spring mechanism 195, as illustrated in FIG. 14. The spring mechanism 195 is shown in a window view in FIG. 14 for illustrative purposes only. The loop 134 is connected to the spring mechanism 195 such that the loop 134 is biased distally, or outwardly, from the lead body 128. The spring 195 can optionally be coupled to a cord 180 extending through the lumen 184. In the embodiment of FIG. 14, a proximally directed tensioning force on the cord 180 flattens the loop 134, thus aiding in removal of the lead assembly 110 from the vessel 25.

Figure 15:
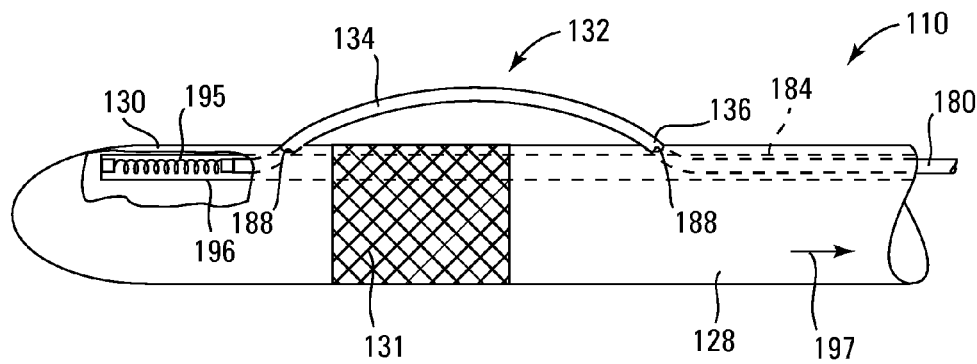
FIG. 15 shows a side view of a distal end of a lead assembly according to another embodiment of the present invention.

In the embodiment shown in FIG. 15, the spring 195 is located at the distal tip 130 of the lead assembly 110 and surrounding a portion 196 of the loop 134. The spring 195 pushes the loop 134 distally or outwardly. In the illustrated embodiment, the loop 134 can optionally be coupled to a cord 180 extending through the lumen 184. As discussed with respect to FIG. 14, application of a proximally directed tensioning force to the cord 180 flattens the loop 134, thereby aiding in removal of the lead assembly 110 from the vessel 25. In an alternative embodiment, the lead assembly does not include the spring 195. The loop biasing feature 132 itself can be stiff enough to provide a biasing force. In this embodiment, the loop 134 can be optionally coupled to a cord 180 extending through a lumen 184 for lead removal as described with respect to FIG. 14. The lead assembly 110 may include multiple loops 134 and the loops 134 may be preformed with multiple curvatures. The loop biasing features 132 may include any combination of necked down regions 146, holes 147, or notches 149.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A lead assembly configured for placement in a coronary vessel of a heart, the coronary vessel having a pericardial wall portion and a myocardial wall portion, the lead assembly comprising:

a lead body extending from a proximal end adapted for coupling to a pulse generator to a distal end adapted for implantation in the heart;

a pace/sense electrode positioned on an outer surface of the lead body, the pace/sense electrode including a first portion on a first side of the lead body; and a loop biasing feature located along the lead body, the loop biasing feature including a resilient loop disposed on, and running in a longitudinal direction along, a second side of the lead body, the resilient loop having a first collapsed configuration, a second expanded configuration, a proximal end, a distal end, a collar for coupling the loop biasing feature to the lead body and a necked down region providing a predefined break location disposed adjacent the distal end of the resilient loop, wherein the resilient loop in the second expanded configuration forms a loop spaced from the second side of the lead body, the resilient loop in the second configuration adapted to push the second side of the lead body away from the pericardial wall and push the first side of the lead body toward the myocardial wall;

wherein the lead body includes a groove for accommodating the collar.

2. The lead assembly of claim 1 wherein the loop biasing feature further includes a fixation structure.

3. The lead assembly of claim 1 wherein the loop biasing feature further includes a plurality of resilient loops.

4. The lead assembly of claim 3 wherein the lead body includes a distal location and at least two of the resilient loops are located at the distal location and are positioned around a circumference of the lead body.

5. The lead assembly of claim 1 wherein the necked down region has a predetermined width so that the loop biasing feature breaks at a desired axial force.

6. The lead assembly of claim 1 wherein the loop biasing feature defines a tissue in-growth area extending from a portion of the pericardial wall to the lead body.

7. The lead assembly of claim 1, wherein the resilient loop is attached to the collar and the collar is disposed around a portion of the lead body within the groove.

8. A lead assembly for placement in a coronary vessel of the heart, the coronary vessel having a pericardial wall portion and a myocardial wall portion, the lead assembly comprising:

a lead body extending from a proximal end adapted for coupling to a pulse generator to a distal end adapted for implantation in the heart, the lead body including a lumen extending from the proximal end to the distal end;

a pace/sense electrode positioned at the distal end of the lead body;

a loop biasing feature located at the distal end of the lead body, the loop biasing feature including a resilient loop positioned to bias a portion of the pace/sense electrode towards the myocardial wall, the loop biasing feature further including a necked down region providing a predefined break location; and a cord coupled to the resilient loop and extending to the proximal end of the lead body, wherein a tensile force applied to the cord causes the resilient loop to flatten towards the lead body and a portion of the loop to slide into the lumen.

9. The lead assembly of claim 8 wherein the lead body includes a cord lumen for receiving a portion of the cord.

10. The lead assembly of claim 8 wherein the tensile force further causes an end of the resilient loop to detach from the lead body.

11. The lead assembly of claim 8 wherein the loop biasing feature defines a tissue in-growth area extending from a portion of the pericardial wall to the lead body.

12. The lead assembly of claim 8 wherein the lead assembly further includes a spring biasing the resilient loop outwardly from the lead body.

* * * * *